US008043290B2

(12) United States Patent  (10) Patent No.: US 8,043,290 B2
Harrison et al.  (45) Date of Patent:  Oct. 25, 2011

(54) APPARATUS AND METHODS FOR MAGNETIC ALTERATION OF DEFORMITIES

(75) Inventors: Michael R. Harrison, San Francisco, CA (US); Richard J. Fechter, San Rafael, CA (US); Arthur Moran, San Bruno, CA (US)

(73) Assignee: The Regents of the University of California, San Francisco, Oakland, CA (US)

( * ) Notice: Subject to any disclaimer, the term of this patent is extended or adjusted under 35 U.S.C. 154(b) by 1743 days.

(21) Appl. No.: 10/954,995

(22) Filed: Sep. 29, 2004

(65) Prior Publication Data

US 2006/0074448 A1  Apr. 6, 2006

(51) Int. Cl.
*A61B 17/56* (2006.01)
(52) U.S. Cl. ...................... 606/60; 623/18.12
(58) Field of Classification Search ............... 623/18.12; 600/12, 15; 606/60
See application file for complete search history.

(56) References Cited

U.S. PATENT DOCUMENTS

| 3,005,458 | A | * | 10/1961 | Brook et al. ............... 606/106 |
| 3,648,372 | A | * | 3/1972 | Kirschenbaum ............ 433/5 |
| 3,890,953 | A | | 6/1975 | Kraus et al. |
| 3,939,821 | A | | 2/1976 | Roth |
| 3,986,493 | A | * | 10/1976 | Hendren, III ............. 600/12 |
| 4,029,091 | A | * | 6/1977 | von Bezold et al. ........ 606/33 |
| 4,063,561 | A | * | 12/1977 | McKenna ............... 128/207.15 |
| 4,266,533 | A | | 5/1981 | Ryaby et al. |
| 4,340,038 | A | | 7/1982 | McKean |
| 4,552,134 | A | * | 11/1985 | Binard ..................... 600/13 |
| 4,896,668 | A | * | 1/1990 | Popoff et al. ............ 606/74 |
| 4,932,951 | A | | 6/1990 | Liboff et al. |
| 5,014,699 | A | | 5/1991 | Pollack et al. |
| 5,458,558 | A | | 10/1995 | Liboff et al. |
| 5,595,563 | A | | 1/1997 | Moisdon |
| 5,690,656 | A | | 11/1997 | Cope et al. |
| 6,006,756 | A | * | 12/1999 | Shadduck ............... 128/899 |
| 6,024,759 | A | | 2/2000 | Nuss et al. |

(Continued)

FOREIGN PATENT DOCUMENTS

SU  806005 B  *  2/1981

OTHER PUBLICATIONS

Harrison MR, Estefan-Ventura D, Fechter R, Moran AM Jr, Christensen D., Magnetic Mini-Mover Procedure for pectus excavatum: I. Development, design, and simulations for feasibility and safety., J Pediatr Surg. Jan. 2007;42(1):81-5; discussion 85-6.*

(Continued)

*Primary Examiner* — Thomas C. Barrett
*Assistant Examiner* — Michael Araj
(74) *Attorney, Agent, or Firm* — Lumen Patent Firm

(57) ABSTRACT

Methods and apparatus for incrementally manipulating an internal body member of a patient are disclosed. The apparatus has a magnetic implant adapted to be received on a location of the body member, a platform external to the patient, and a magnetic member coupled to the platform, wherein the magnetic member generates a magnetic force between the implant and the platform to incrementally manipulate the body member. The implant and external magnetic member are preferably rare earth magnets or an array of rare earth magnets, and are configured to generate an attractive or repulsive force between the implant and the platform to reposition, reorient, deform, or lengthen the body member.

28 Claims, 18 Drawing Sheets

U.S. PATENT DOCUMENTS

| | | | |
|---|---|---|---|
| 6,099,542 | A | 8/2000 | Cohn et al. |
| 6,292,680 | B1 | 9/2001 | Somogyi et al. |
| 6,306,075 | B1 * | 10/2001 | Shadduck ................ 600/12 |
| 6,352,543 | B1 | 3/2002 | Cole |
| 6,387,096 | B1 | 5/2002 | Hyde, Jr. |
| 6,569,166 | B2 | 5/2003 | Gonzalez |
| 6,652,540 | B1 | 11/2003 | Cole et al. |
| 6,656,194 | B1 | 12/2003 | Gannoe et al. |
| 6,669,709 | B1 | 12/2003 | Cohn et al. |
| 6,719,768 | B1 | 4/2004 | Cole et al. |
| 6,802,847 | B1 | 10/2004 | Carson et al. |
| 7,001,402 | B2 | 2/2006 | Yencho |
| 7,135,022 | B2 * | 11/2006 | Kosashvili et al. ............ 606/63 |
| 2002/0072758 | A1 | 6/2002 | Reo et al. |
| 2002/0103495 | A1 | 8/2002 | Cole |
| 2003/0144682 | A1 * | 7/2003 | Qureshi et al. ............... 606/191 |
| 2004/0030395 | A1 * | 2/2004 | Blunn et al. ............... 623/18.12 |
| 2004/0116945 | A1 | 6/2004 | Sharkawy et al. |
| 2004/0122334 | A1 * | 6/2004 | Yamashiro ................... 600/534 |
| 2004/0215214 | A1 | 10/2004 | Crews et al. |
| 2005/0021059 | A1 | 1/2005 | Cole et al. |
| 2005/0080439 | A1 | 4/2005 | Carson et al. |
| 2005/0228412 | A1 | 10/2005 | Surti |
| 2006/0036267 | A1 | 2/2006 | Saadat et al. |
| 2006/0282106 | A1 | 12/2006 | Cole et al. |
| 2007/0010834 | A1 | 1/2007 | Sharkawy et al. |
| 2007/0156055 | A1 * | 7/2007 | Royalty ........................ 600/509 |
| 2007/0250162 | A1 * | 10/2007 | Royalty ....................... 623/3.11 |

OTHER PUBLICATIONS

Isakov et al., A new method of surgical treatment of funnel chest with help of permanent magnets, 1980, Chirurgie Pediatrique, Masson, 21(5), pp. 361-362.*

Leonard, Arnold M.D., "Surgical Corrective Procedure for Pectus Excavatum and Pectus Carinatum", http://www.pectusdeformity.com, downloaded from Internet Jun. 8, 2004, pp. 1-5.

Pittman, T. et al. Cranial vault molding by the transcutaneous activation of implanted magnets. Pediatr. Neurosurg., 1997, vol. 27, pp. 78-83.

* cited by examiner

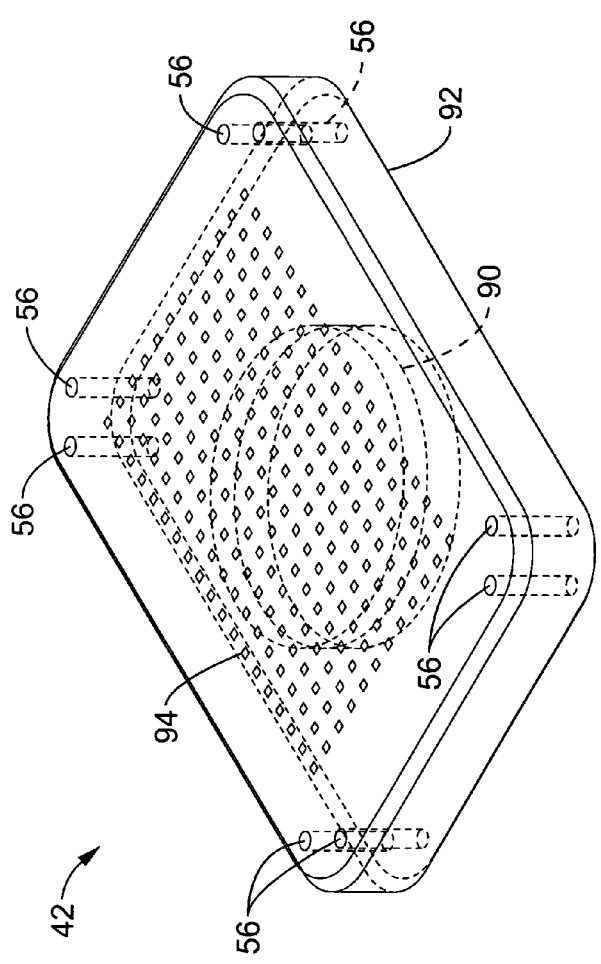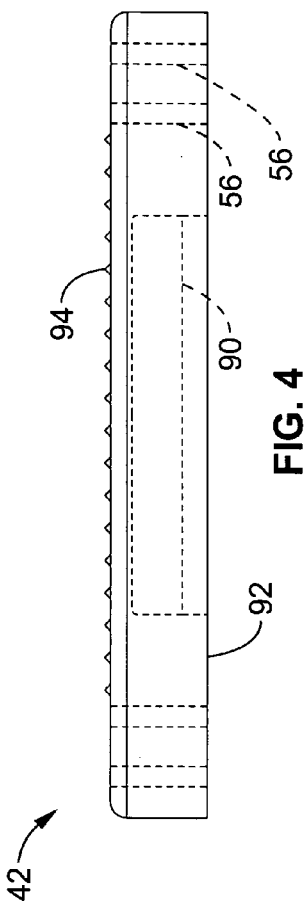

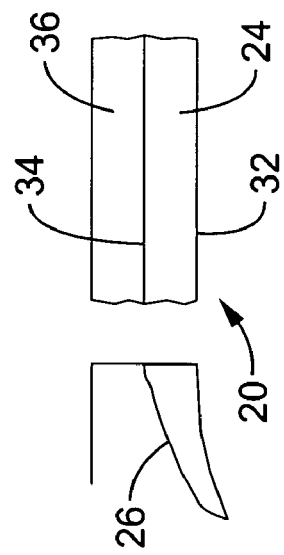
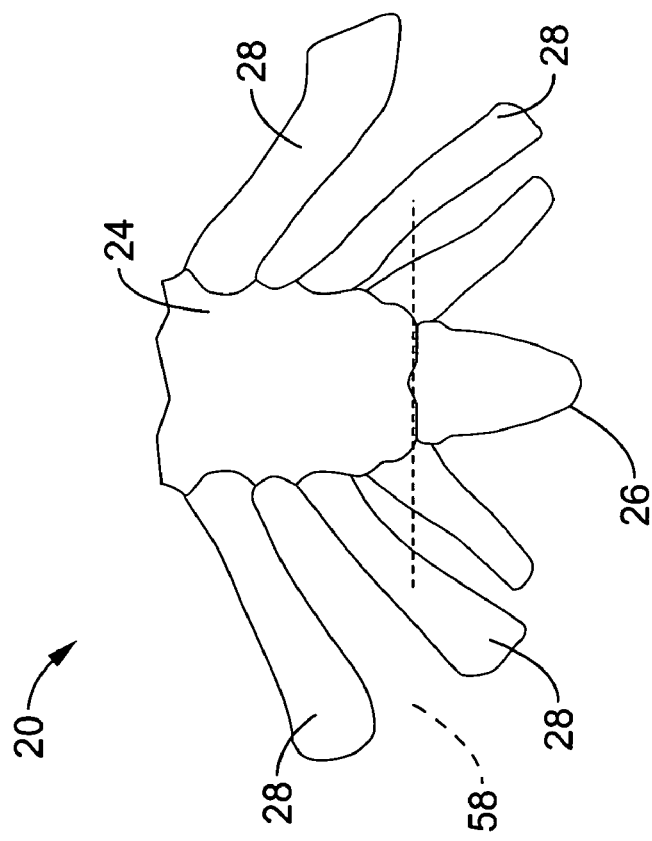

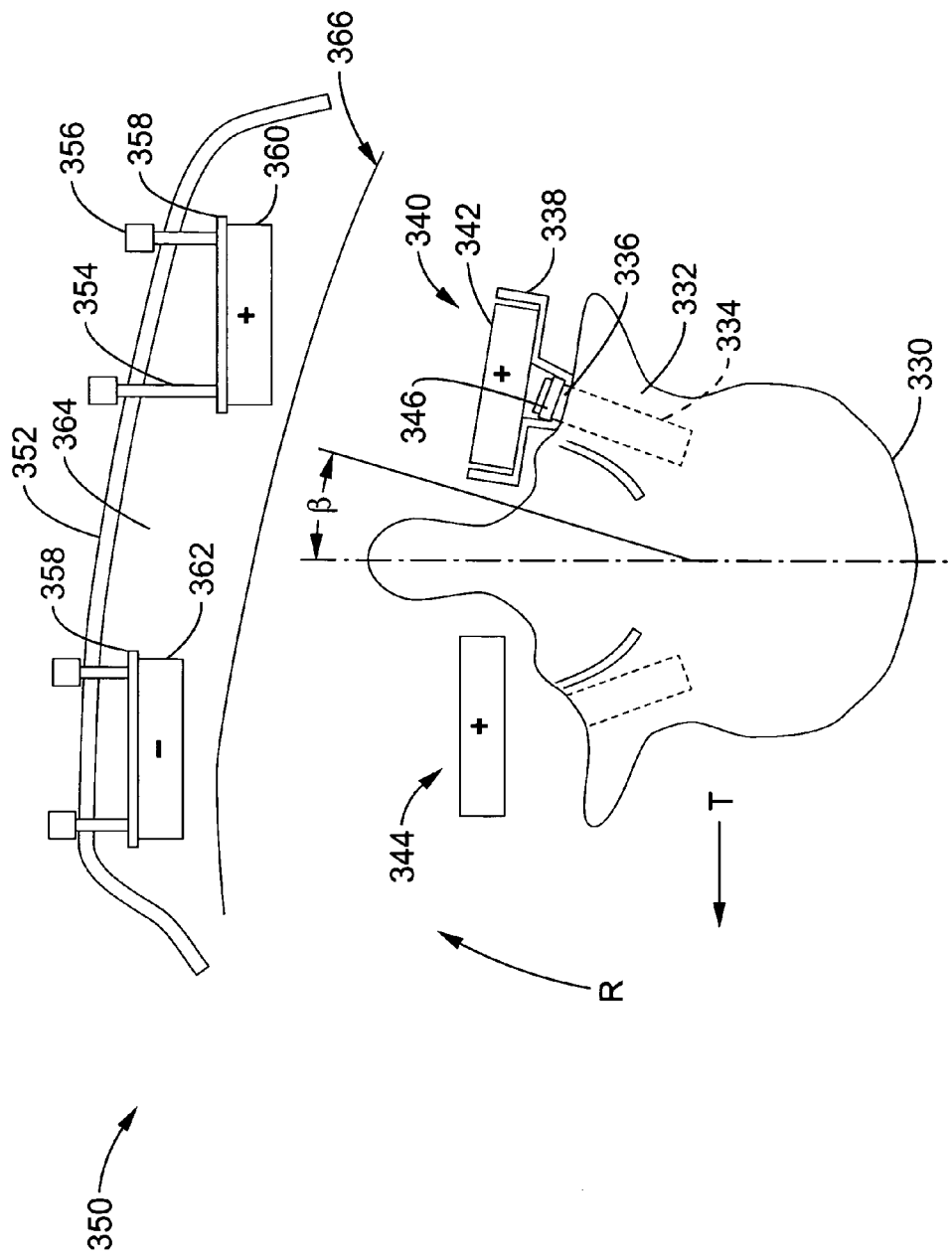

APPARATUS AND METHODS FOR MAGNETIC ALTERATION OF DEFORMITIES

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to apparatus and methods for magnetically manipulating and/or deforming bone structures and more particularly to performing a surgical procedure on a patient having a skeletal deformity.

2. Description of Related Art

Anatomical deformities occur in the general populous in a number of different forms and from a variety of causes. Examples of skeletal deformities include, pectus excavatum, scoliosis, club feet, and numerous forms of skeletal dysplasia. These conditions are treated in a variety of different manners from braces to surgery, with sometimes minimal efficacy.

The defect known as pectus excavatum, or funnel chest, is a congenital anomaly of the anterior chest wall. The excavatum defect is characterized by a deep depression of the sternum, usually involving the lower half or two thirds of the sternum, with the most recessed or deepest area at the junction of the chest and the abdomen. The lower 4-6 costal or rib cartilages dip backward abnormally to increase the deformity or depression and push the sternum posterior or backward toward the spine. Also, in many of these deformities, the sternum is asymmetric or it courses to the right or left in this depression. In many instances, the depression is on the right side.

Pectus excavatum with significant deformity occurs in approximately 1 out of every 2000 births. The deformity may be present at birth but is often noted after several years of age and usually worsens during rapid growth around puberty. Because of the pressure of the sternum and cartilages, defect also pushes the midline structures so that the lungs are compressed from side to side and the heart (right ventricle) is compressed. Severe lesions have a major effect on thoracic volume and pulmonary function but the principal motivation for repair is the deformity itself. It does occur in families and thus, is inherited in many instances. Other problems, especially in the muscle and skeletal system, also may accompany this defect. In approximately $\frac{1}{5}$ of the patients, scoliosis is present. The regression or any improvement in this defect rarely occurs because of the fixation of the cartilages and the ligaments. When one takes a deep breath or inspires, the defect is usually accentuated.

Pectus excavatum can be repaired surgically using an open approach in which the malformed costal cartilages are resected and the sternum forcibly held in place with a metal strut. In another approach, described in U.S. Pat. No. 6,024,759, the sternum is forced into a corrected position often under great tension, and held in place with a metal strut. Both can achieve good results but at the cost of considerable morbidity: an operation under general anesthesia followed by a 4-7 day hospital stay required for pain control usually by continuous epidural analgesia. Several more weeks of moderate to severe discomfort are typical and complications from the sternum held forcibly against the metal strut are not infrequent. It is necessary to leave the bar in place for a year or more before it is removed in another procedure. Total cost usually reimbursed by third party payers averages more than $30,000.

The problem with all currently available pectus excavatum surgical repairs is that they attempt to achieve immediate total correction and fixation often under considerable tension. A better approach would be the gradual step-by-step correction of the deformity by applying a smaller force over a longer period of time.

Another skeletal deformity, scoliosis, is a condition in which an individual has an abnormal spine curvature. Generally, some curvature in the neck, upper trunk and lower trunk is normal. However, when there are abnormal side-to-side (lateral) curves in the spinal column, the patient is generally diagnosed as having as scoliosis.

Orthopaedic braces are typically used to prevent further spinal deformity in children with curve magnitudes within the range of 25 to 40 degrees. If these children already have curvatures of these magnitudes and still have a substantial amount of skeletal growth left, then bracing is a viable option. The intent of bracing, however, is to prevent further deformity, and is generally not used to correct the existing curvature or to make the curve disappear.

Surgery is an option used primarily for severe scoliosis (curves greater than 45 degrees) or for curves that do not respond to bracing. The two primary goals for surgery are to stop a curve from progressing during adult life and to diminish spinal deformity.

Although there are different techniques and methods used today for scoliosis surgery, all of them involve fairly invasive procedures with considerable patient morbidity. One frequently performed surgery involves posterior spinal fusion with instrumentation and bone grafting, which is performed through the patient's back. During this surgery, the surgeon attaches a metal rod to each side of the patient's spine by anchor's attached to the vertebral bodies. The spine is then fused with a bone graft. The operation usually takes several hours and the patient is typically hospitalized for a week or more. Most patients are not able to return to school or for several weeks after the surgery and cannot perform some pre-operative activities for up to four to six months.

Another surgery option for scoliosis is an anterior approach, wherein the surgery is conducted through the chest walls instead of entering through the patient's back. During this procedure, the surgeon makes incisions in the patient's side, deflates the lung and removes a rib in order to reach the spine. The anterior spinal approach generally has quicker patient rehabilitation, but usually requires bracing for several months after this surgery.

For these reasons it would be desirable to provide improved apparatus and methods for repositioning bone structures, by applying a corrective force to the bone structure, which could be gradually adjusted much like orthodontic tooth braces.

It would be further desirable to provide a device that applies a corrective force to reposition a body member without a mechanical force that requires piercing of the skin, thereby limiting the specter of infection and wound problems.

In addition, it would be desirable to provide a device for repositioning bones structures having tension-sensing technology to allow measurement of the force applied to correct all types of asymmetric deformities and allow protection of skin against pressure damage.

It would further be desirable to provide improved devices and methods for minimally invasively treating pectus excavatum.

In addition, it would be desirable to provide improved devices and methods for minimally invasively treating scoliosis.

At least some of these objectives will be met with the inventions described hereinafter.

BRIEF SUMMARY OF THE INVENTION

The present invention comprises apparatus and methods for altering the position, orientation, growth or development of body parts and organs by magnetic forces to apply a steady sustained force over time. The invention uses magnetic force fields that may be used to correct a number of anatomic deformities, including, but not limited to: pectum excavetum, pectus carinatum, scoliosis, club feet, cranial/facial anomalies or defects, skeletal dysplasias, cartilaginous deformities/dysphasia, and joint deformities/dysphasia. The invention may also be used to incrementally lengthen bone or apply bone compression to promote healing.

An aspect of the invention is an apparatus for incrementally manipulating an internal body member of a patient. In one embodiment, the apparatus comprises magnetic implant adapted to be received on a location of the body member, a platform external to the patient, and a magnetic member coupled to the platform, wherein the magnetic member generates a magnetic force between the implant and the platform to incrementally manipulate the body member. The implant and external magnetic member preferably comprise a rare earth magnet or array of rare earth magnets, and are configured to generate an attractive or repulsive force between the implant and the platform to reposition, reorient, deform, or lengthen the body member.

In one aspect of the invention, the implant is adapted to be received on a location of the sternum to treat pectus excavatum. In this configuration the platform comprises a chest plate adapted to be positioned exterior to the patient's chest. The magnetic member is coupled to the chest plate to generate an attractive force between the implant and the chest plate to incrementally reposition the sternum.

The implant is preferably adapted to be received on a posterior surface on the sternum. The implant generally comprises an internal magnet and a casing to enclose the internal magnet. The casing may be made from any rigid biocompatible material capable of withstanding the forces of the magnet without significant deformation, such as high-grade medical epoxy or similar material used in the art.

In a preferred embodiment, the implant is attached to the sternum using a plurality of sutures, wherein the sutures are looped through a plurality of holes in the implant casing and around the sternum to attach the implant to the posterior surface of the sternum.

In one embodiment, the platform chest plate generally has a concave inner surface to allow the sternum to deform outwardly from the chest. The platform may also have an adjustable stage coupled to the chest plate, wherein the magnetic member is mounted on the stage. A plurality of adjustment members may be coupled to the stage to adjust the orientation and position of the magnetic member with the implant.

In another embodiment of the invention, a plurality of sensors and a strain gauge may be coupled to the chest plate, with the strain gauge measuring the force applied to one or more locations on the platform.

In most cases the attractive force of the magnets support the chest plate to the patient's chest. However, a chest strap may also be used to support the chest plate to the patient's chest.

In another aspect of the invention, the implant is adapted to be received on a location of a vertebrae of the patient's spine to treat scoliosis or other spinal disorders. In this configuration, the platform comprises a support adapted to be positioned exterior to the patient's torso. Generally, the magnetic member is coupled to the support such that the magnetic member generates a magnetic force between the implant and the plate to incrementally reposition the spine. The magnetic member and the implant may be configured to generate an attractive or repulsive force between the implant and the magnetic member.

Where the patient has an abnormal curvature of the spine, the implant is preferably configured to be received on a vertebrae located at an apex of the abnormal curvature. The support may be positioned such that the magnetic force incrementally repositions the spine to remove the abnormal curvature. The implant and the magnetic member may also be configured to impart a torsional force on the vertebrae to incrementally reorient the spine.

In one embodiment, a bone screw is threaded into the vertebrae to rigidly couple the implant to the vertebrae.

According to another aspect of the invention, a method for incrementally repositioning an internal body member of a patient comprises installing a magnetically responsive implant to a location on the internal body member; positioning a platform exterior the patient to generate a magnetic field, the magnetic field effecting an magnetic force between the implant and the platform, and manipulating the body member to a first state as a result of the generated magnetic force.

In a preferred embodiment, the method also includes adjusting the magnetic field to one or more intermediate settings, manipulating the body member to one or more intermediate state as a result of the attractive force generated by the one or more adjusted magnetic field settings, adjusting the magnetic field to a final setting; and manipulating the body member to a final state as a result of the attractive force generated by the final magnetic field setting.

The step of generating a magnetic field may comprise generating an attractive or repulsive force between the implant and the platform. The body member may be manipulated by repositioning the body member to a first position, deforming the body member to a first shape, or lengthening the body member to a first length. Repositioning the sternum may comprise deforming one or more cartilages connected to the sternum as a result of the attractive force, or deforming the shape of the sternum as a result of the attractive force.

In one aspect of the invention, manipulating a body member comprises manipulating the patient's sternum. In such a configuration, installing a magnetically responsive implant comprises attaching an internal magnet to a posterior location on the sternum. Positioning a platform is achieved by manipulating a stage housing an external magnet, the stage being coupled to a chest plate. A plurality of adjustment members may be used to adjust the position and orientation of the external magnet with respect to the internal magnet, thereby effecting the magnitude and direction of the magnetic force between the platform and the implant.

In one aspect of the invention, manipulating a body member comprises manipulating a vertebrae of the patient. In such a configuration, installing a magnetically responsive implant comprises attaching an internal magnet to a location on the vertebrae. The vertebrae may be manipulated by adjusting the magnetic field between the implant and the platform to incrementally reposition the spine. The magnetic field may be adjusted to generate an attractive or repulsive force between the implant and the platform to incrementally reposition the spine. Where the spine has an abnormal curvature, the implant is installed on a vertebrae located at an apex of the abnormal curvature. In such a configuration the vertebrae may be manipulated to incrementally reposition the spine to remove the abnormal curvature. A torsional force may also be imparted on the vertebrae to incrementally reorient the spine.

In a preferred embodiment, installing the implant comprises boring a hole in a pedicle of the vertebrae, and threading a pedicle screw into the pedicle, the pedicle screw configured to rigidly couple the implant to the vertebrae.

In another aspect of the invention method is disclosed for performing a pectus excavatum procedure on a patient having a deformed sternum. The method comprises attaching a magnetically responsive implant to a location on the sternum, and positioning a chest plate exterior the patient's chest to generate a magnetic field, wherein the magnetic field effects an attractive force between the implant and the chest plate. The implant generally comprises a first magnet housed in a biocompatible casing.

The first magnet may be attached to a posterior surface on the sternum by incising a section of the patient's skin over the patient's sternum, separating the xiphoid process from the sternum, dissecting under the sternum and securing the first magnet to the posterior surface of the sternum. One method for securing the first magnet to the sternum comprises drilling a plurality of holes from an anterior location on the sternum to a posterior location on the sternum, and looping a plurality of sutures through the holes in the sternum and through a plurality of holes in the casing housing the first magnet.

According to yet another aspect of the invention, a method for incrementally repositioning a patient's sternum is disclosed. The method comprises installing a magnetically responsive implant to a location on the sternum, positioning a chest plate exterior the patient's chest to generate a magnetic field, wherein the magnetic field effects an attractive force between the implant and the chest plate, repositioning the patient's sternum to a first position as a result of the generated magnetic force, manipulating the magnetic field to one or more intermediate settings, repositioning the patient's sternum to one or more intermediate positions as a result of the attractive force generated by the one or more manipulated magnetic field settings, manipulating the magnetic field to a final setting, and repositioning the patient's sternum to a final position as a result of the attractive force generated by the final magnetic field setting.

According to a further aspect of the invention, an apparatus for incrementally manipulating an internal body member of a patient comprises a magnetically responsive implant adapted to be received on a location of the body member, the implant responsive to a magnetic field, and means for generating an attractive force between the implant and a platform external to the patient to manipulate the body member. The device may further comprise means for adjusting the magnitude and direction of the magnetic force applied between the platform and the implant. The device also has means for securing the implant to a location on the body member.

In a preferred embodiment, the apparatus has a means for detecting the force applied to the platform at a plurality of locations on the platform, such as a strain gauge. The strain gauge may also configured to measure the force at a plurality of locations on the platform.

According to yet another aspect of the invention, a method for incrementally repositioning an internal body member of a patient comprises installing a magnetically responsive implant to a location on the internal body member, positioning a platform exterior the patient to generate a magnetic field, the magnetic field effecting a magnetic force between the implant and the platform, measuring the magnetic force between the implant and the platform; adjusting the platform to tune the magnetic force applied between the implant and the platform; and manipulating the body member to a first state as a result of the generated magnetic force.

In an alternative embodiment of the present invention, an apparatus for manipulating one or more internal body members is disclosed. The apparatus comprises a first elongate member having a driving end and a receiving end, wherein the receiving end of the first member having a recess extending toward the driving end. The apparatus also has a second elongate member having a driving end and a receiving end, the receiving end of the second member having a recess extending toward the driving end. The second member is sized such that the receiving end of the second member is slideably received within the receiving end of the first member. The apparatus further comprises a first magnet coupled to the first member, and a second magnet coupled to the second member, wherein the first and second magnets are configured to repel each other such that an outward magnetic force is generated to the driving ends of the first and second members. The first and second magnets may be positioned within the recesses to change the magnitude of the force generated between the first and second magnets. The first and second magnets may also be configured such that rotation of the first magnet with respect to the second magnet changes the magnitude of the force generated between the first and second magnets.

According to another aspect of the invention, an apparatus for intermittently delivering a force to a body member to incrementally manipulate the body member comprises an implant adapted to be received on a location of the body member, the implant responsive to a magnetic field, a platform external to the patient, and a magnetic member coupled to the platform, wherein the magnetic member generates a magnetic force between the implant and the platform to incrementally manipulate the body member, the magnetic member and the implant configured such that rotation of the magnetic member varies the magnetic force between the implant and the platform.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only, and where like reference numbers denote like elements:

FIG. 3 shows an embodiment of the implant of the present invention.

FIG. 4 is a side view of the implant of FIG. 3.

FIG. 5. is a schematic view of a sternum.

FIG. 6. is a cross-sectional view of a sternum with the xiphoid separated from the sternum body.

Figure 7:
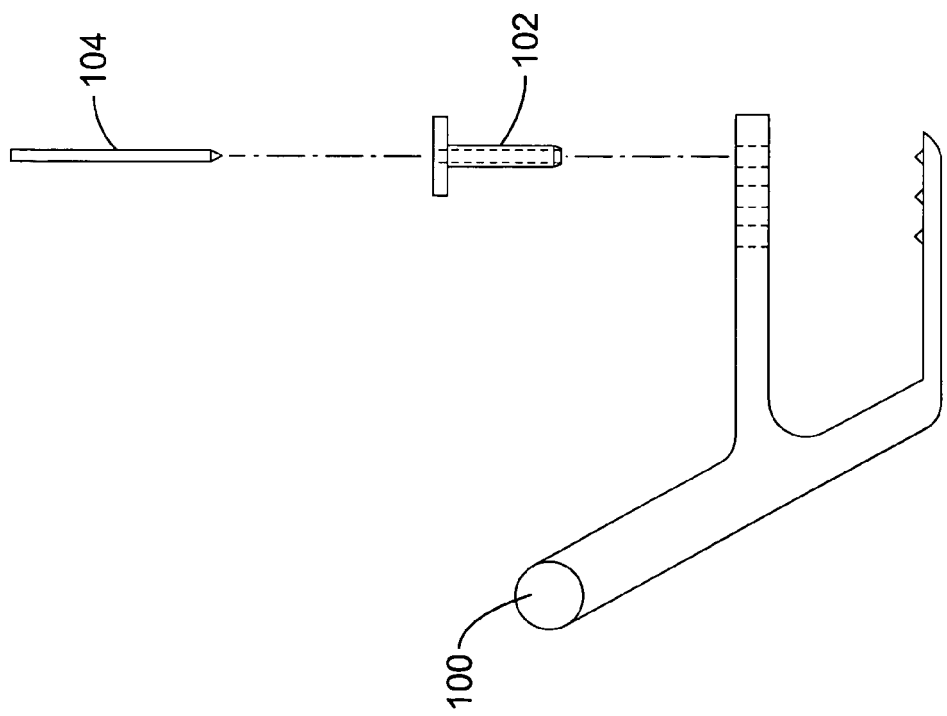

FIG. 7 is an implant drill guide according to the present invention.

Figure 8:
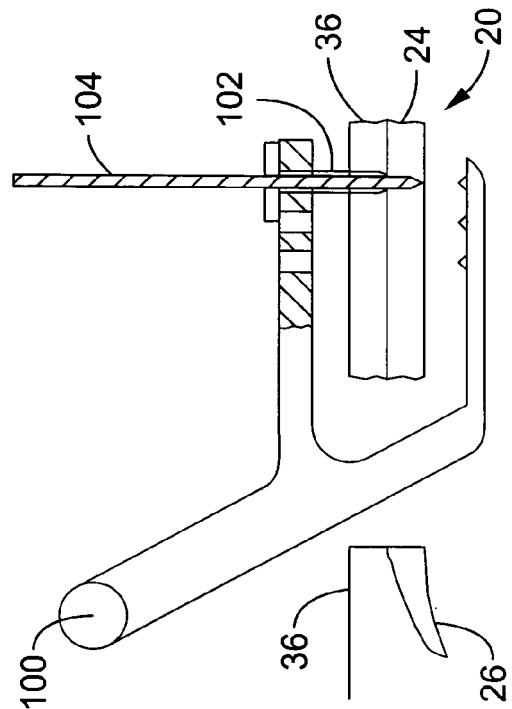

FIG. 8 shows the drill guide of FIG. 7 installed over the sternum.

Figures 9, 10:
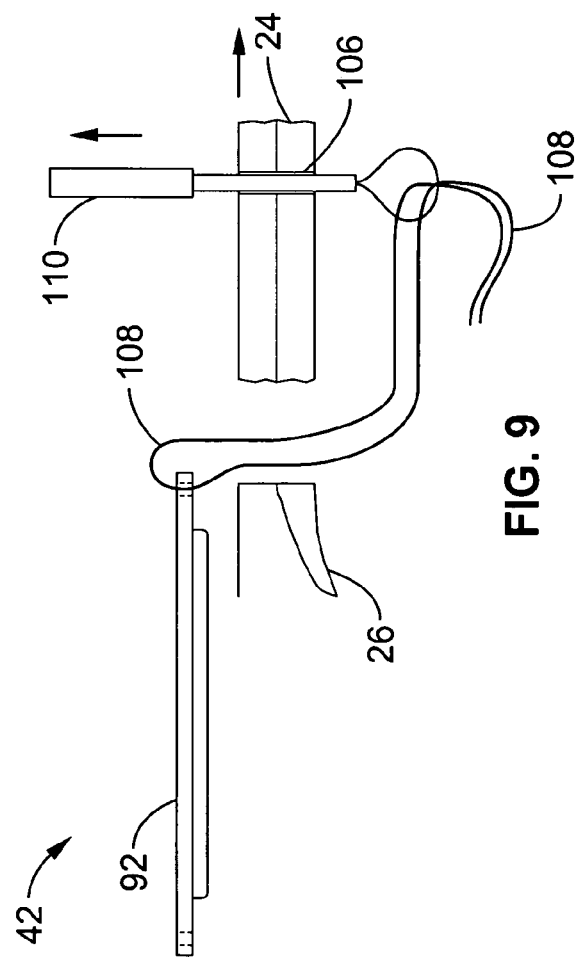

FIG. 9 illustrates a preferred method for installing a portion of the implant to the posterior surface of the sternum.

FIG. 10 illustrates a portion of the drill guide of FIG. 7 positioned over a second location on the sternum.

Figure 11:
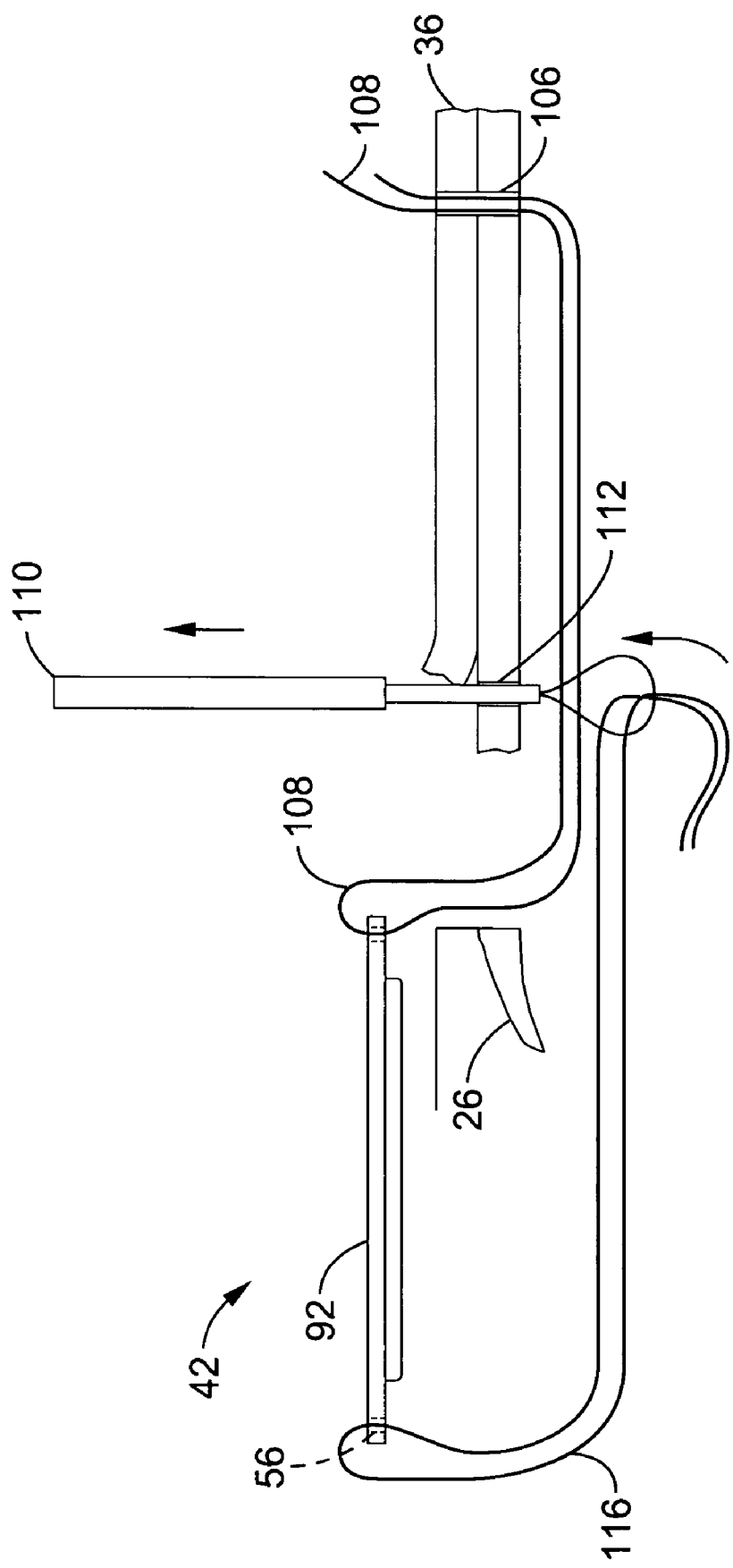

FIG. 11 illustrates a preferred method for installing a second portion of the implant to the posterior surface of the sternum.

Figure 12:
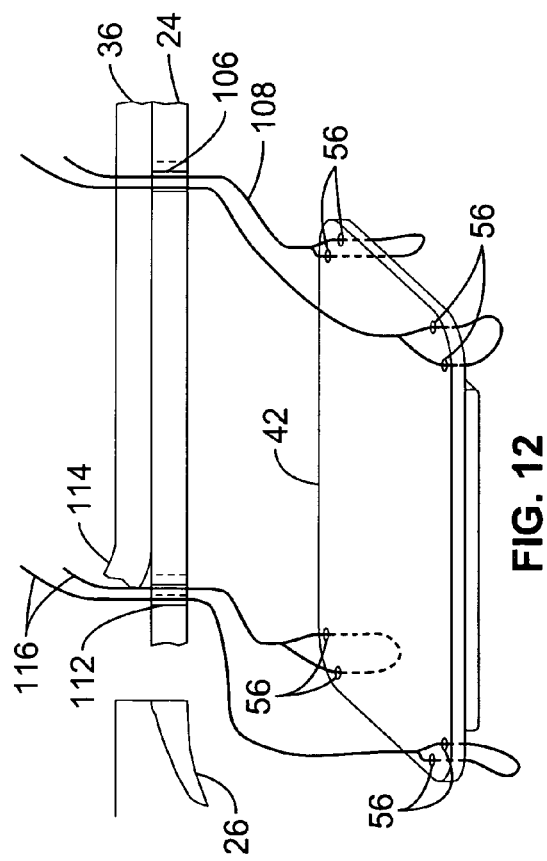

FIG. 12 is another view of the method of FIG. 11.

Figure 13:
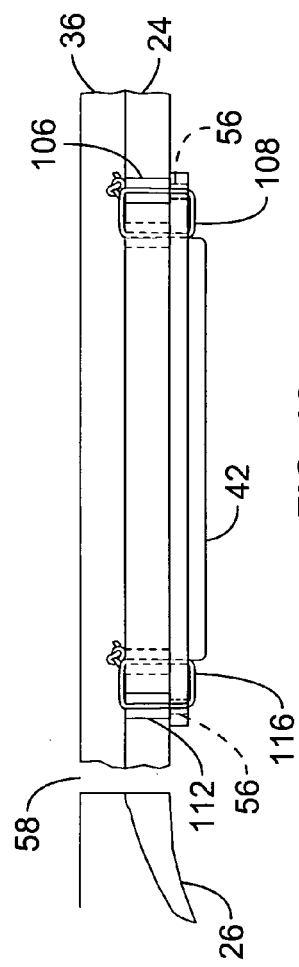

FIG. 13 shows the implant according to the present invention installed on the posterior surface of the sternum.

Figure 14:
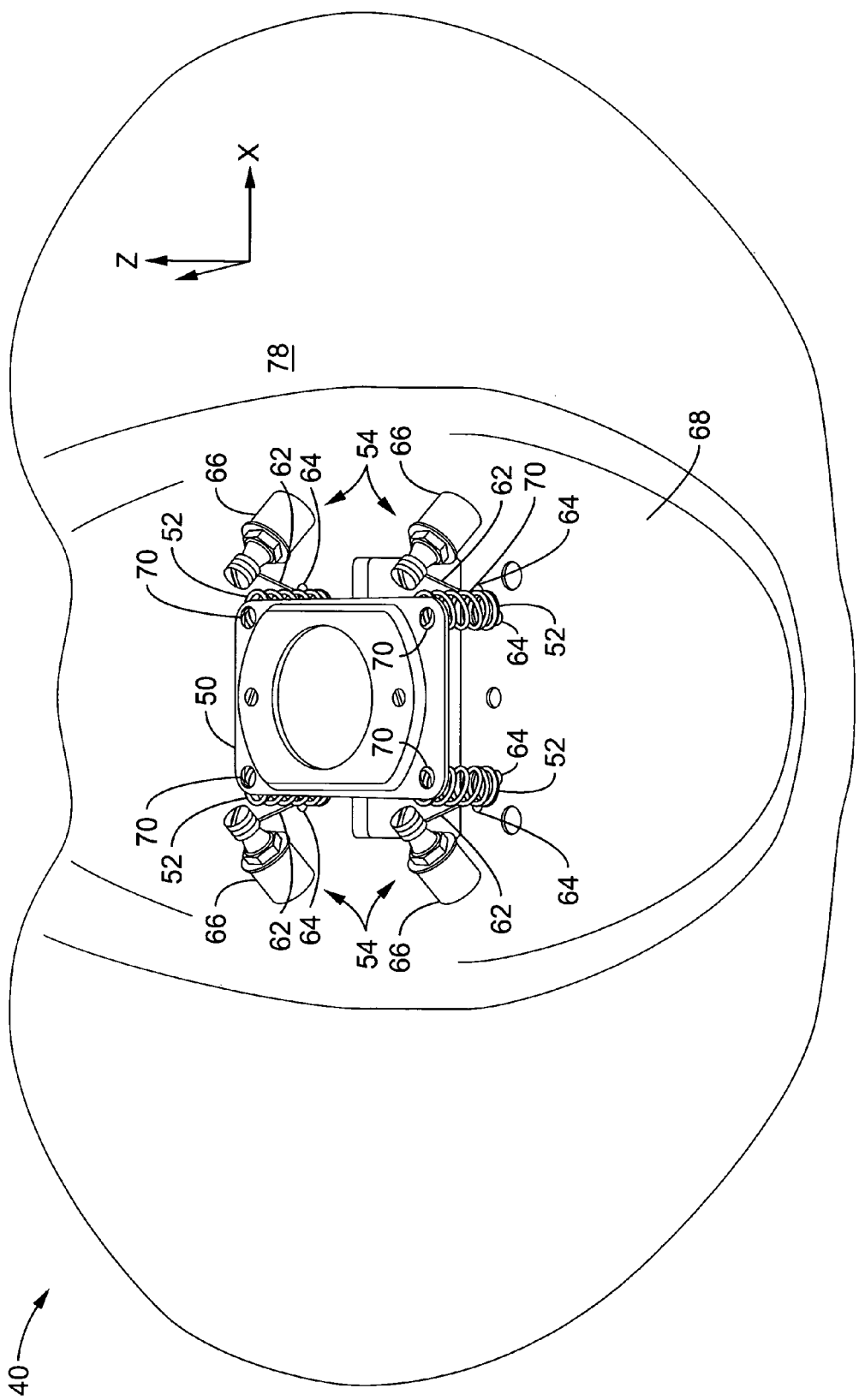

FIG. 14 is a view of the underside of an embodiment of the platform according to the present invention.

Figure 15:
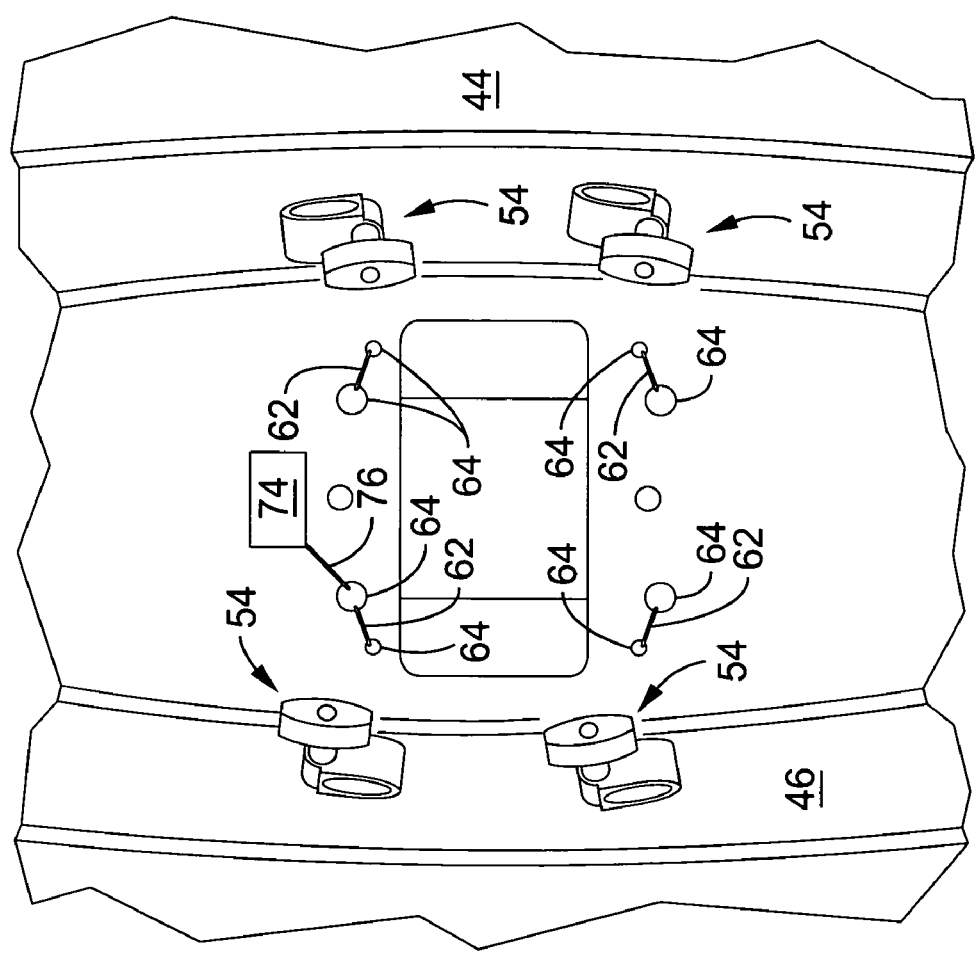

FIG. 15 is a view of the top of the platform of FIG. 14.

Figure 16:
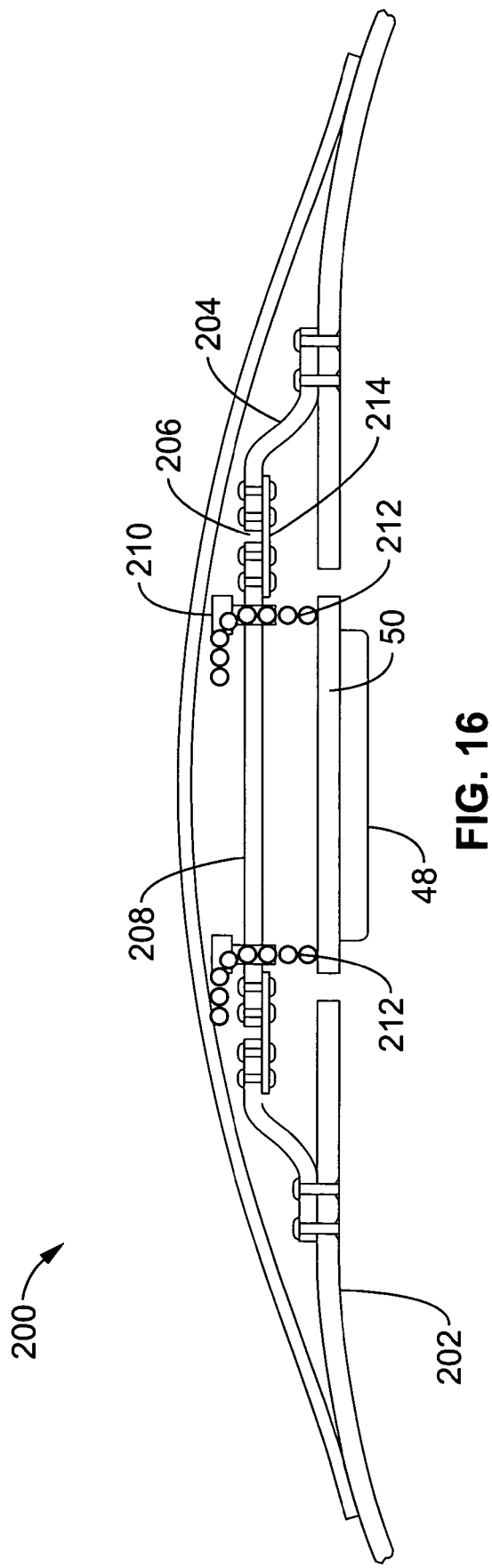

FIG. 16 is a side view of another embodiment of the platform of the present invention.

Figure 17:
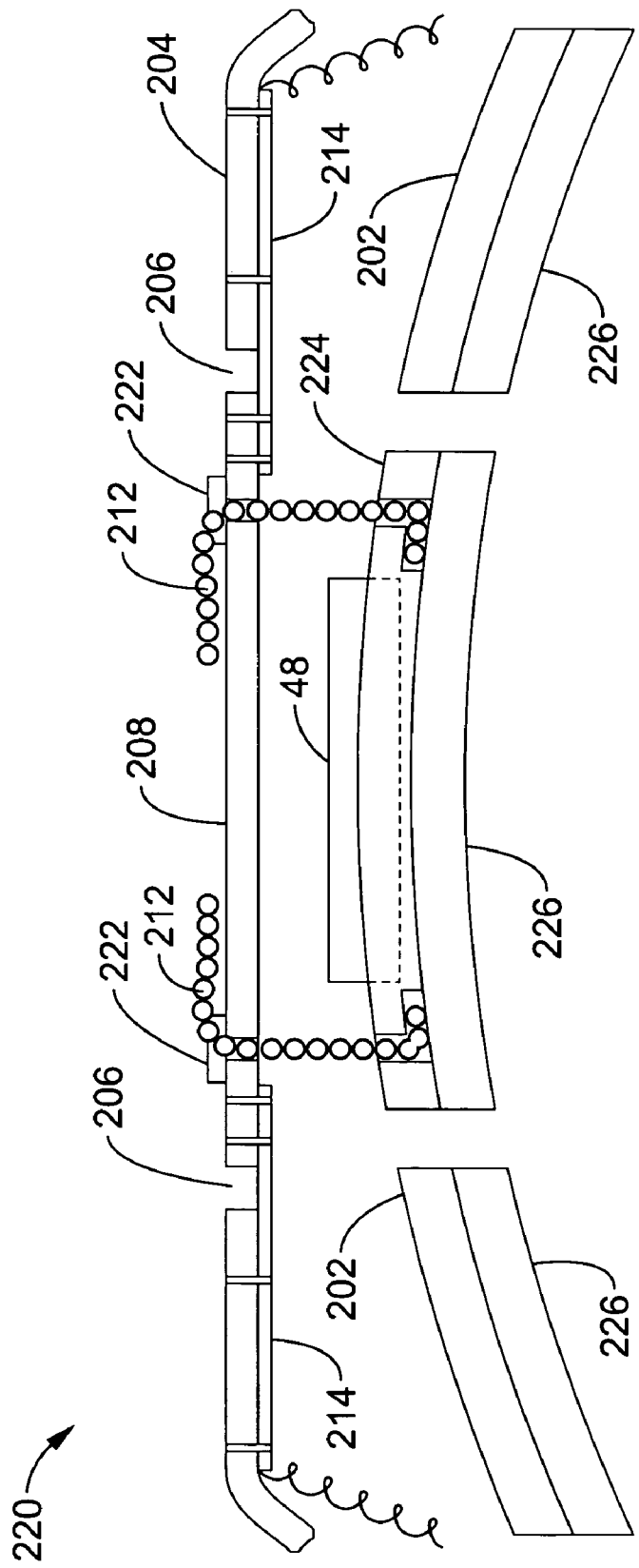

FIG. 17 is a side of another embodiment of the platform of the present invention.

Figure 18B:
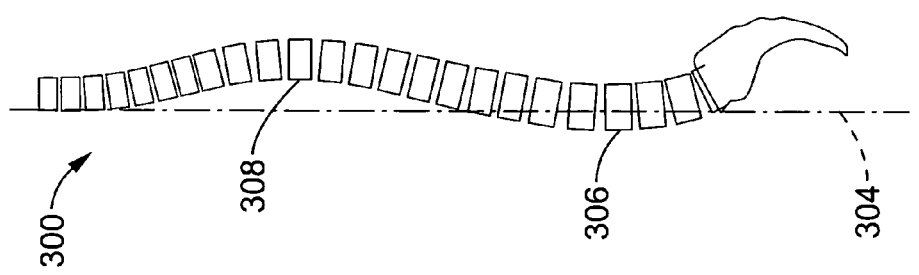
Figure 18A:
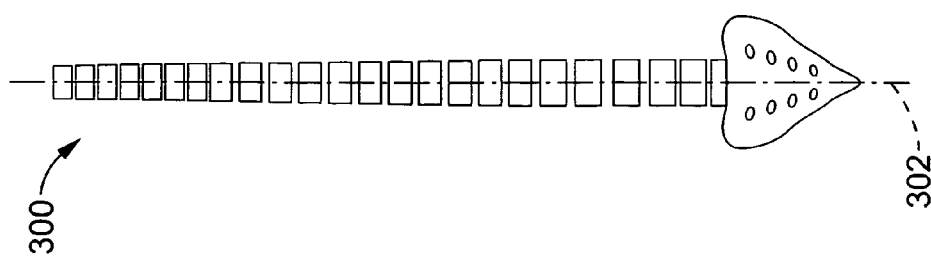

FIG. 18A is an anterior view of the human spine.

FIG. 18B is a lateral view of the human spine.

FIG. 19A-D illustrate various abnormal curvatures of the spine due to scoliosis.

Figure 20:
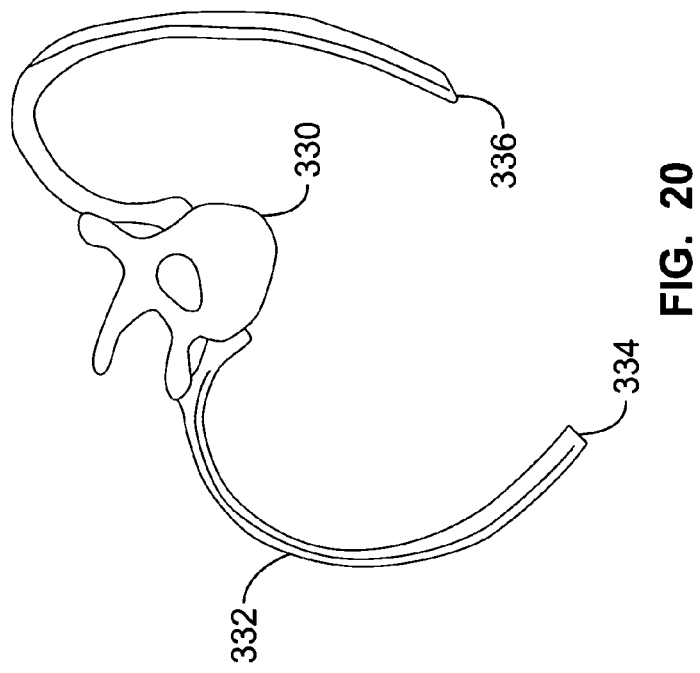

FIG. 20 illustrates abnormal rotation of the vertebrae of the spine as a result of scoliosis.

FIG. 21 illustrates another embodiment of the invention for treating scoliosis.

Figure 22:
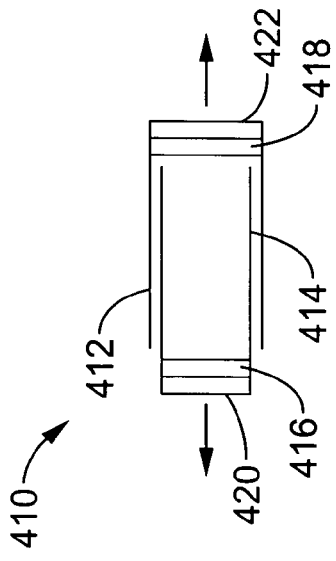

FIG. 22 illustrates an alternative embodiment for delivering a pulsed magnetic field to a body member.

Figure 23:
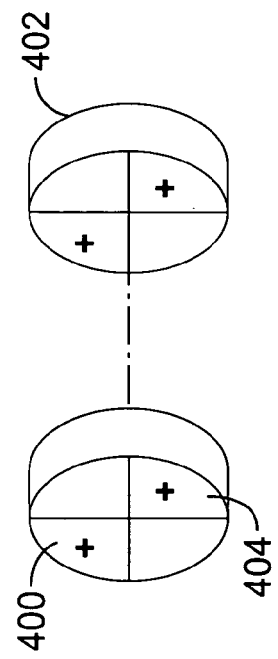

FIG. 23 is a schematic view of an alternative embodiment for delivering a repulsive force to a body member.

Figure 24:
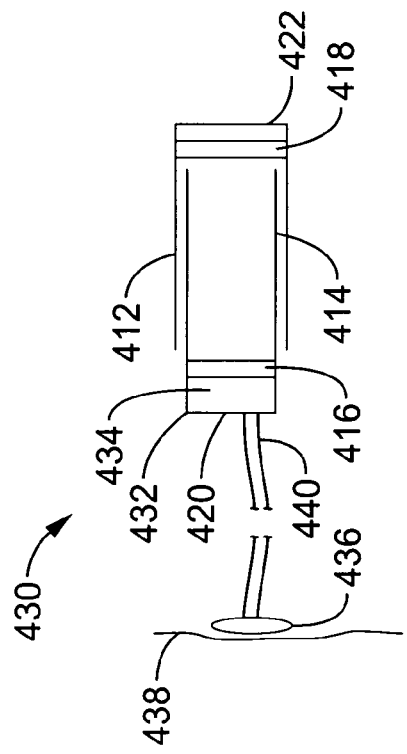

FIG. 24 is a schematic view of the device of FIG. 23 with a fluid pump.

Figure 25:
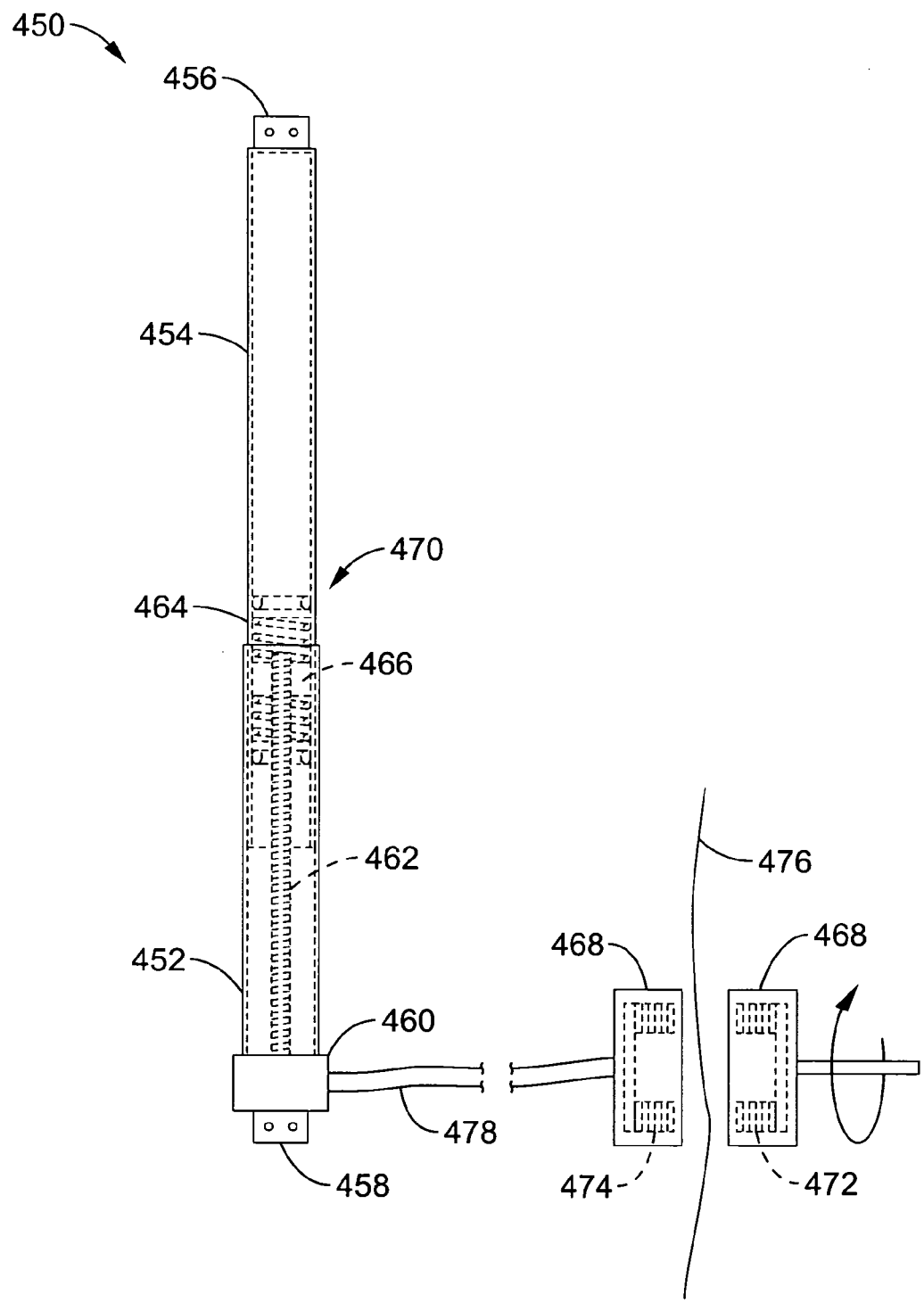

FIG. 25 illustrates an alternative embodiment of a repulsion device incorporating a mechanical jackscrew.

Figure 26:
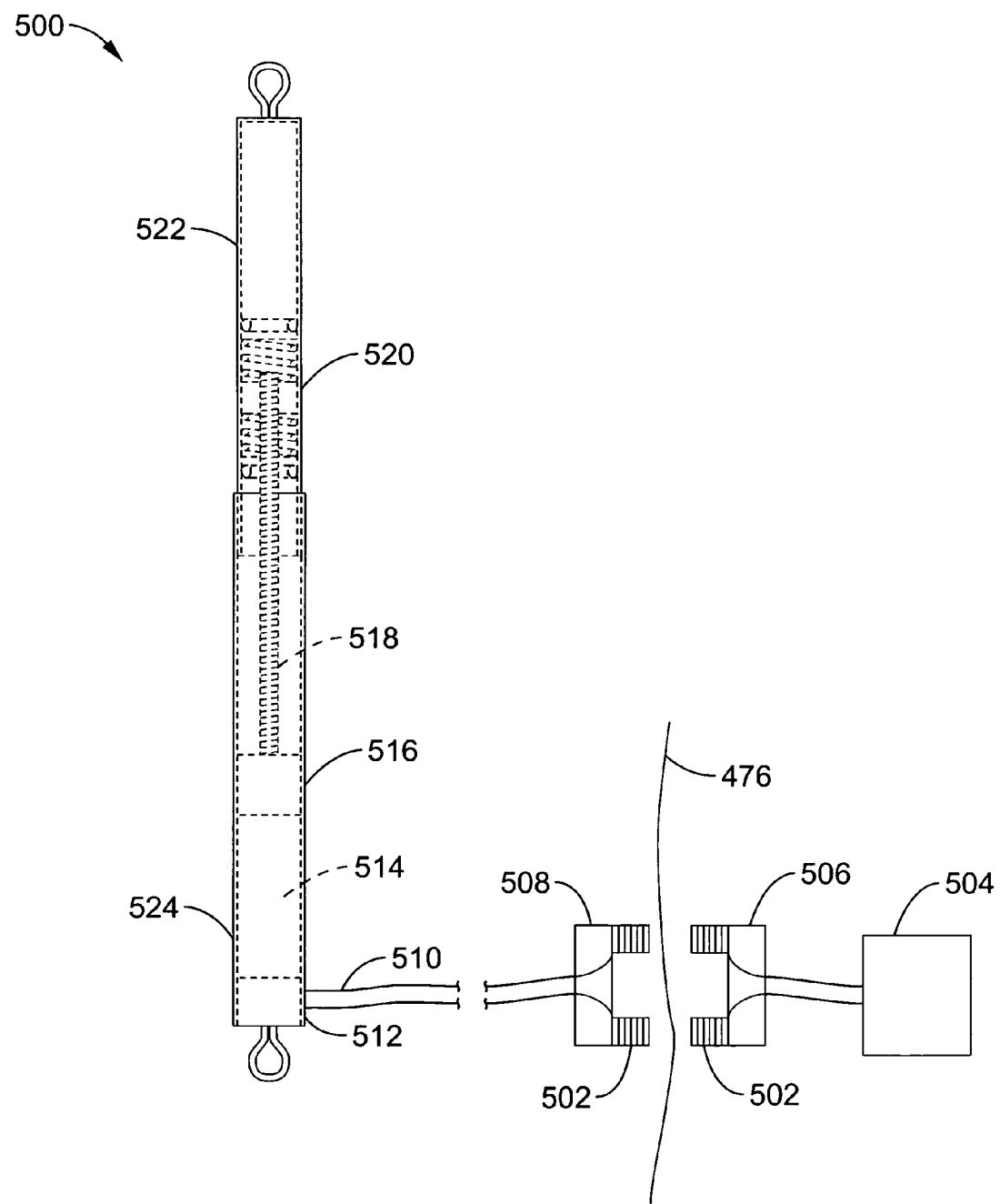

FIG. 26 illustrates an alternative embodiment of a repulsion device incorporating an electric jackscrew.

DETAILED DESCRIPTION OF THE INVENTION

Referring more specifically to the drawings, for illustrative purposes the present invention is embodied in the apparatus generally shown in FIG. 1 through FIG. 17 and FIGS. 21-26. It will be appreciated that the apparatus may vary as to configuration and as to details of the parts, and that the methods may vary as to the specific steps and sequence, without departing from the basic concepts as disclosed herein.

The present invention utilizes a system in which a small magnet is implanted in cooperation with an internal body member to apply a corrective force to the body member by virtue of its attraction to an adjustable magnet in an external device that is comfortable and cosmetically pleasing.

Small rare earth metal magnets can produce considerable force and can be manipulated in terms of size, shape and position. This force can be used to alter growth and development of skeletal structure and soft tissue. The biology of tissue response to force has been well studied. Clinical application of this powerful biologic principle has been limited by the difficulties of applying force through external bracing or through internal pins manipulated by external devices (e.g., bone lengthening through distraction osteogenesis). Magnetic force fields can be used to apply force to implanted magnets attached to an internal structure without violating the skin and soft tissue. The magnetic force field can be manipulated externally to adjust the direction, strength and speed at which the deformity is corrected.

1. Pectus Excavetum

Figure 1:
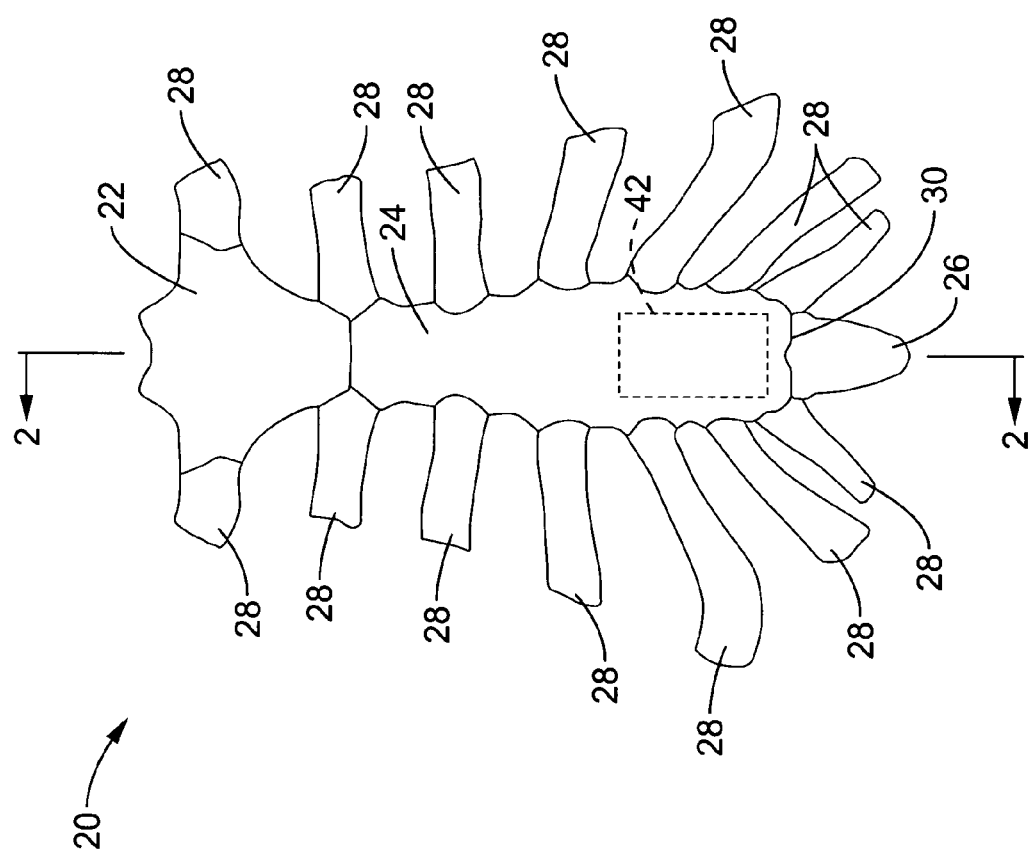
FIG. 1 is a schematic view of a human sternum with an implant according to the present invention installed under the sternum.

FIGS. 1-16 illustrate a preferred embodiment of the invention relating to the correction of pectus excavetum. FIG. 1 illustrates a schematic, anterior view of a human sternum 20. The sternum 20 is an elongated, flatted bone, forming the middle portion of the anterior wall of the thorax. The sternum 20 generally consists of three parts: the manubrium 22, which at its upper end supports the clavicles (not shown); the body or gladiolis 24, which interfaces at its upper end with the lower end of the manubrium 22, and the xiphoid process 26, which interfaces at its upper end with the lower end of the gladiolis 24 at junction 30. The margins of sternum 20 articulate with the first of seven pairs of ribs 28.

Figure 2:
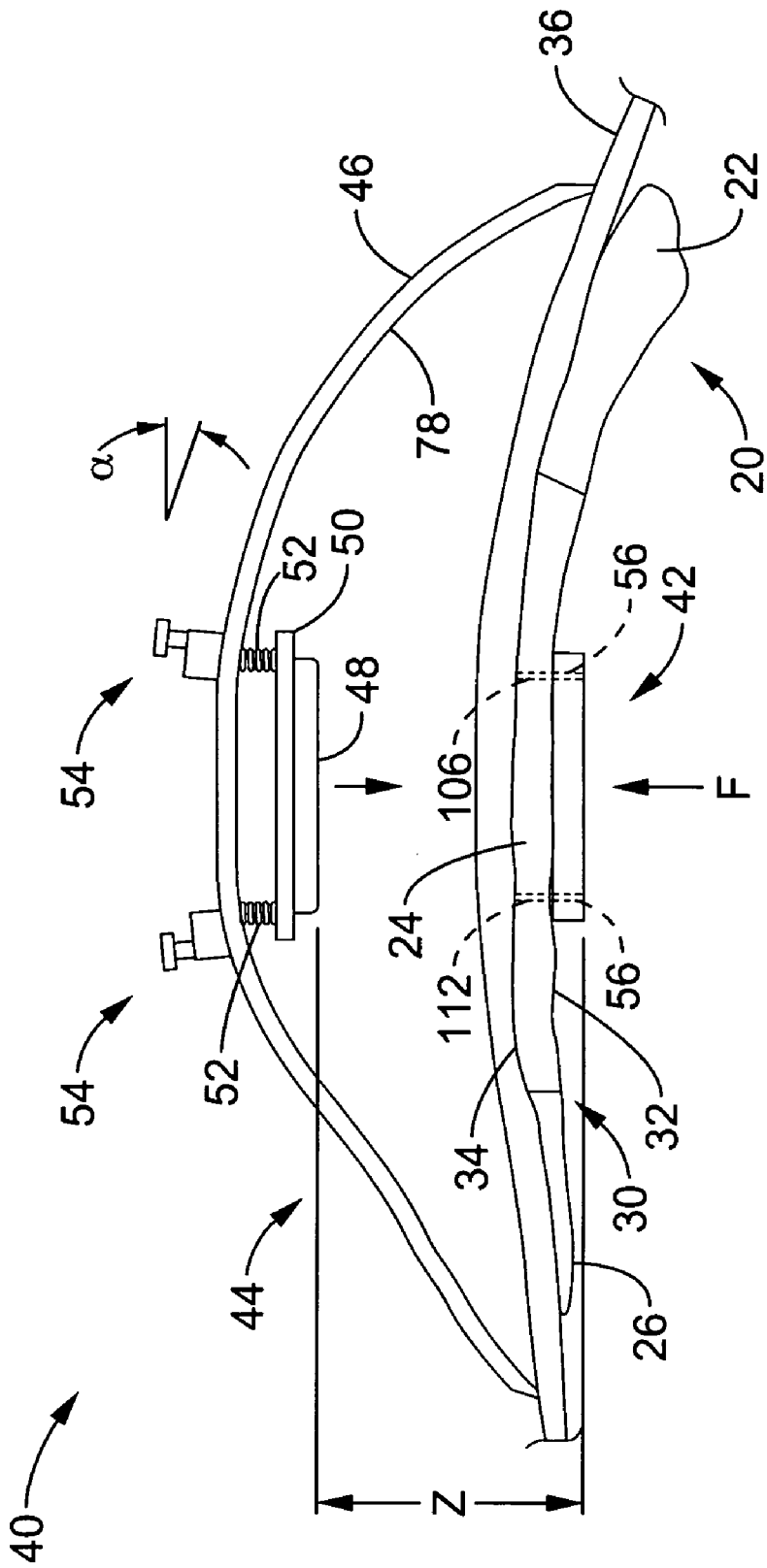
FIG. 2 is a cross-sectional schematic view of the platform of the present invention installed over a patient's chest and an implant installed under the sternum.

As shown in FIG. 1 and illustrated as a cross-sectional view of a corrected patient's chest in FIG. 2, a magnetic substernal implant 42 may be installed on the posterior surface 32 the body 24 of the sternum 20, just above the xiphoid process 26. Illustrated in greater detail in FIG. 3, the implant 42 preferably comprises a rare earth magnet 90, or an array of rare earth magnets housed in casing 92. The casing 92 may comprise any biocompatible material such as medical grade epoxy or suitable material used in the art. Casing 92 preferably has mounting holes 56 for fixation at each corner. The casing 92 may also have a plurality of protrusions 94 to enhance the attachment of the implant 42 with the sternum 20.

The magnetic implant 42 is sized to fit comfortably behind the sternum. An exemplary implant may 3 inches long, 2½ inches wide and 3/16 thick. However, the size of the implant may vary according to patient anatomy.

FIG. 2 and FIGS. 5-13 illustrate an exemplary method of surgically installing the implant 42. A 3 cm substernal transverse incision 58 is made through the patient's skin 36. The ziphoid process 26 is then separated from the lower sternum body 24 and a pocket is bluntly dissected behind the posterior surface 32 of the sternum, as illustrated in FIG. 6.

The implant 42 is attached to the posterior surface of the sternum with sutury passed through the holes 112 in the sternum illustrated in FIG. 2. Using laparoscopic or arthroscopic visualization, a drill guide 100 is inserted and positioned over the proximal end of the sternum body 24, as shown in FIGS. 7 and 8. A small stab wound is made into skin 36, and the drill sleeve 102 is inserted through the guide 100. The sternum 20 is then drilled under direct visualization to bore one or more distal bores 106 from the anterior surface 34 of the sternum through to the posterior surface 32. Distal bores 106 preferably line up with the corresponding mounting holes 56 in casing 92.

Referring now to FIG. 9, a distal suture 108 is looped through one of the mount holes 56 of casing 92. The distal suture 108 preferably comprises a heavy braided suture commonly used in the art, e.g. #2 or #5 ticron. The suture is then fed under the sternum 20 and a suture retriever 110, such as a Hewson type, is used to pull the distal suture 108 through the corresponding distal bore 106 in the sternum body 24 and the anterior skin stab wound. The process is repeated for the second corner of the distal end of the casing 92.

Referring now to FIG. 10, the proximal end 114 of skin 36 and subcutaneous tissues from the anterior sternum proximal to the sterno-xiphoid junction 58 are pulled back to expose the proximal end of the sternum body 24. The drill guide 100 is moved transversely along the sternum body 24 to the exposed portion of the sternum under proximal end 114. Once sufficient exposure is obtained, one or more proximal bores 112 are drilled under direct vision through the sternum anteriorly-to-posteriorly, thus providing anchoring points for all corners of the casing 92.

Now referring to FIGS. 11 and 12, a proximal suture 116 is looped through one of the mount holes 56 on the proximal end of casing 92. The suture is then fed under the sternum 20 and suture retriever 110 is used to pull both ends of the proximal suture 116 through the corresponding proximal bore 112 in the sternum body 24. The process is repeated for the second corner of the proximal end of the casing 92.

As seen in FIG. 12, both sets of proximal and distal sutures 116, 108 are pulled to guide the implant 42 up behind the sternum 20 and maintain the apposition of the casing 92 to the sternum 20 with traction on the sutures.

Referring now to FIG. 13, the proximal sutures 116 are tied down firmly over the sternal bone bridge to secure the implant 20 to the proximal surface 32 of the sternum. Under direct vision, the process is repeated for the distal sutures 108.

Although FIGS. 9-13 illustrate a preferred embodiment using suture to fasten the implant 42 to the sternum 20, it is appreciated that any number of different fastening means commonly known in the art may be used to secure the implant 42. For example, bolts (not shown) may be passed through bores 106, 112, threaded into threaded mounting holes 56 of casing 92 and torqued down to secure the implant 42 to the posterior surface 32 of the sternum 20.

Surgical placement generally requires a brief outpatient general anesthesia. The procedure takes about 30 minutes and requires minimal post-operative analgesia.

FIGS. 2 and 14-17 illustrate several embodiments of an external magnet platform of the present invention for treating pectus excavatum. FIGS. 14 and 15 show an embodiment having a platform 40 configured to be worn over a patient's chest. Platform 40 comprises a chest plate 44 sized according to the patient's anatomy. Generally, a mold is made of the individual's chest deformity. From this the desired end point position of the sternum and chest wall shape are molded to create the chest plate 44. FIG. 14 is a bottom view of platform 40, showing the underside 78 of chest plate 44. In addition to being contoured to comfortably rest on the patient's chest, the underside 78 of the chest plate is cut away to create cavity 68 that allows the chest to expand outward as a result of treatment.

In a first configuration, an external magnet 48 is hung from the underside 78 of the chest plate 44 by a plurality of adjustment cables 62. External magnet 48 is preferably a rare earth magnet, or array of rare earth magnets. The external magnet has an adjustable stage, or mounting plate 50, which has a plurality of holes 70 to secure cables 62. As illustrated in FIGS. 14 and 15, the magnet 48 is hung with 4 cables. However, other configurations, such as a three cable design (not shown), may also be used. The cables 62 are coupled to the chest plate via adjustment members 54. Cables 62 lead from the magnet plate 50 out to the exterior surface 46 and back through to the underside of the chest plate via through holes 64 to terminate at adjustment member 54. One or more biasing springs 52 may be imposed between the chest plate 44 and the magnet 48, creating a tensile force on cables 62 so that the magnet is biased to the furthest orientation away from the chest plate 44 that is allowed from the cables' length.

By turning adjustment member 54 from the top of the chest plate illustrated in FIG. 15, the cable 62 may be shortened, thereby advancing one corner of the magnet plate 50 upward toward the chest plate 44. By rotating the adjustment member in the opposite direction, the cable is extended, thereby advancing one corner of the magnet plate 50 toward from the patient's chest and away from the chest plate 44. When all the adjustment members are moved the same increment, the magnet will translate toward or away from the patient's chest in the Z axis (see FIGS. 2 and 14). The magnet may also be rotated angle $\theta$ about the X or Y axis by manipulating the adjustment members 54 to lengthen or shorten one or more cables 62 with respect to the remaining cables.

The external magnet 48 and the implant magnet 90 are configured so that their opposite poles face each other, thereby generating an attractive force between the two magnets. By manipulating the distance of the external magnet 48 from the chest plate 44 in the Z direction, the amount of force applied to the internal magnet can be incrementally tuned or adjusted. By manipulating the orientation of the external magnet 48 with respect to the chest plate 44 in the X and Y directions, the direction of force applied to the internal magnet can be incrementally adjusted.

The chest plate 44 is preferably comprised of a rigid material, such as a rigid thermoplastic or polymer or steel reinforced polymer, that does not deform as a result of the magnetic forces, allowing external magnet 48 to remain stationary with respect to the patient's chest. As a result of the constant force applied from the external magnet 48, the implant 42 imposes a corrective outward force F on the posterior surface 32 of the sternum 20. This outward force incrementally repositions/deforms the sternum 20 to move outward from the patient's chest cavity. By adjusting the angle of the external magnet in the X and Y directions, the force generated on the implant 42 may be directed to orient the sternum in the X and Y axes as well to correct asymmetric lesions.

An initial adjustment of the platform is made after the implant is placed in the outpatient surgical procedure. When the sternum 20 and implant 42 move toward the external magnet 48, the force generated between the magnets increases. If this force becomes too great and becomes uncomfortable for the patient, the magnet may be retracted toward the chest plate 44, thereby returning the magnetic force to the optimum comfort level for the patient. This process may be repeated for a number of intermediary steps, until the sternum 20 is gradually repositioned and/or deformed toward the desired final position and orientation.

The platform 40 may also include a strain gauge 74, or other force measuring means, to accurately determine the force being generated by the magnets. Strain gauge 74 may be connected via lead wires 76 to various points on the magnet plate 50 so that the pressure on each quadrant of the magnet may be accurately assessed. Strain gauge 74 may also comprise an LCD display (not shown) so that the patient or physician may readily assess whether the external magnet 48 is properly oriented, and adjust the magnet if need be.

The platform 40 is held in place by the magnetic pull between the two magnets, and in addition may be secured in place with a loose elastic band (not shown) around the chest. The principal force holding the platform 40 in place is the magnetic field itself. The patient may adjust the platform 40 to comfort and thus ensure against pressure damage to soft tissue. The patient may be taught to how to manipulate the external magnet 48 up and down to adjust and balance the force pulling the sternum 20 outward.

To provide extra comfort to the patient, and prevent the any unwanted manipulation of the adjustment members, a cover, such as that shown in FIG. 16, may be provided to cover the chest plate while the platform is being worn.

A preferred embodiment of the invention incorporating a bridged platform 200 is illustrated in FIGS. 16 and 17. Platform 200 has a chest plate 202 having a support 204 with opening 206 at it center. Chest plate 202 and support 204 may be separate pieces fastened together as shown in FIG. 16, or one integrated piece (not shown). Load member 208 is positioned in the opening 206 of support 204, and is bridged by a plurality of thin beam force sensors 214.

Load member 208 has a plurality of adjustment members 210 that retain magnet plate 50 and magnet 48 via a hanging means 212. Adjustment member 210 comprises an in-line screw, such as a jack-screw, lead screw, ball screw, or the like, which is hollowed out to support hanging means 212. As shown in FIGS. 16 and 17, hanging means 212 comprises a ball chain, but may also comprise a cable, wire, or the like. Alternatively, adjustment members 210 may comprise extended screws (not shown) that terminate a ball joint in magnet plate 50.

Adjustment members 210 may be manipulated to lower or raise the magnet 48, or adjust the angle of the magnet, as described in the embodiment of FIGS. 14 and 15. By turning screw 210 clockwise, one quadrant of the external magnet 48 may be precisely lowered to change the angle of the external magnet 48 with respect to the patient's chest, thereby changing the direction of the force applied to the implant 42. By turning all the screws the same clockwise increment, the magnet is lowered to generate a larger attractive force on the implant. Correspondingly, counter-clockwise rotation raises the external magnet to lower the attractive force on the implant 42.

When the platform is placed against the patient's chest, the attractive force between the implant 42 and the external magnet generates a load on load member 208. This load is sensed at all four quadrants by the thin beam force sensors 214. Readings from the sensors 214 are received by a force measuring means, such as the strain gauge 74 illustrated in FIG. 15, to provide accurate data on the force applied at each quadrant of the external magnet. This enables the treating physician or patient to accurately assess corrective force being applied to the sternum, and modify the force if not at the desired level.

FIG. 17 illustrates an alternative embodiment having a platform 220 wherein the adjustment member comprises a clasp 222 for incrementally adjusting the extended length of ball chain 212, which is attached to each corner of the external magnet cradle 224. By changing the position at which the clasp 222 engages the ball chain 212 (similar to adjusting a necklace of bracelet), the height at any one quadrant of the magnet 48 may be changed with respect to the patient's chest to vary the force or direction of the corrective magnetic field. Chest plate 202 and cradle 204 may also have a layer of padding 226 to provide further comfort for the patient.

Over time, the steady gradual force applied to the sternum stretches the ligaments connecting the sternum 20 to the ribs. The sternum 20 itself may also deform as a result of the magnetic forces. The result is a reoriented and/or repositioned sternum without the characteristic depression of the pectus excavatum deformity.

As the sternum 20 moves closer to the external magnet 48, the patient or physician will typically readjust the position of external magnet 48 farther up into the chest plate. This is easily accomplished by adjusting the length of the four ball chains that suspend the magnet cradle 224.

2. Scoliosis

FIGS. 18A and 18B illustrate the curvature of a normal spine 300. The spine is relatively straight in the sagittal plane 302 and has a double curve in the coronal plane 304. As shown below, the thoracic section 308 of the spine is convex posteriorly and the lumbar section 306 of the spine is convex anteriorly. Normally there should be no lateral curvature of the spine about the saggital plane 302.

Figure 19B:
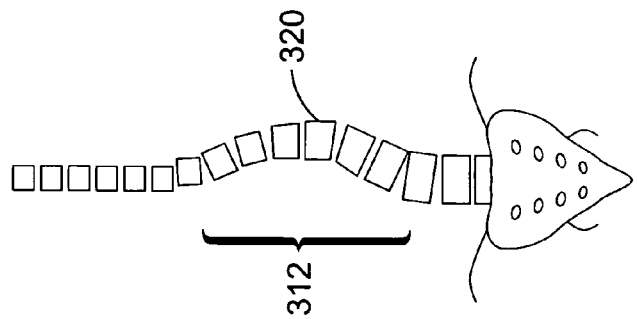
Figure 19A:
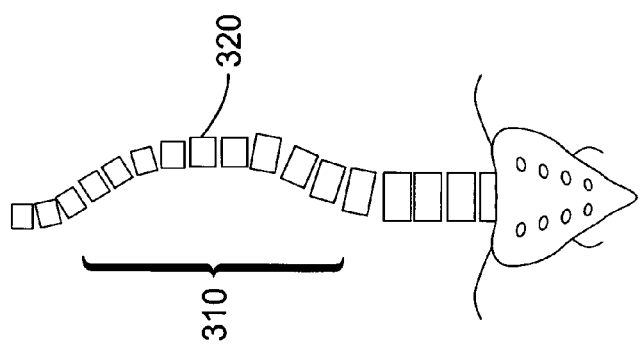
Figure 19D:
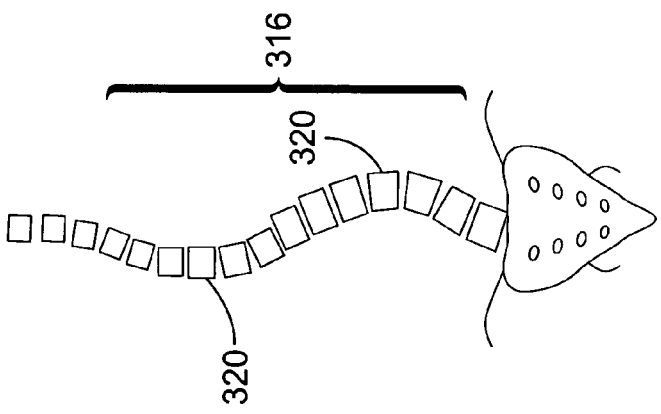
Figure 19C:
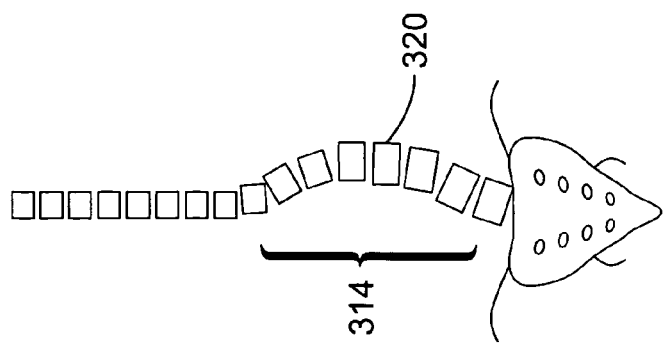

Scoliosis is a deformity that generally comprises by both lateral curvature and vertebral rotation. FIGS. 19A-D illustrate various forms of abnormal lateral curvature of the spine. FIG. 19A shows abnormal thoracic curvature 310. FIG. 19B shows abnormal thoracolumbar curvature 312. FIG. 19C shows abnormal lumbar curvature 314. Finally, some cases involve a double curvature of the spine, as shown in FIG. 19D shows abnormal thoracic curvature.

FIG. 20 illustrates rotation of the spine and corresponding effect on the rib cage 332 as a result of scoliosis. As the disease progresses, the vertebrae 330 and spinous processes in the area of the major curve rotate toward the concavity of the curve. As the vertebral bodies rotate, the spinous processes deviate more and more to the concave side and the ribs follow the rotation of the vertebrae. The posterior ribs on the convex side 336 are pushed posteriorly, causing narrowing of the thoracic cage and the characteristic rib hump seen in thoracic scoliosis. The anterior ribs on the concave side 334 are pushed laterally and anteriorly.

Now referring to FIG. 21, a schematic view of external platform 350 is illustrated with implant 340 installed on vertebrae 330 of the spine. Vertebrae 330 is preferably located at the apex 320 of the abnormal curvature shown in FIGS. 19A-D. In a preferred embodiment implant 340 is anchored to vertebrae 330 via a bone screw 336. Screw 336 may be threaded into a bore 334 in the pedicle 332 of the vertebrae according to commonly used procedures for a variety of spinal conditions, including degenerative disc disease and scoliosis. Examples of such systems are disclosed in U.S. Pat. Nos. 6,648,915; 6,010,503; 5,946,760; 5,863,293; 4,653,481, etc., the entire disclosures of which are incorporated herein by reference.

Once pedicle screw 336 is installed, internal magnet 342 may be fastened to screw 336 via magnet casing 338 and nut 346. Following the same procedure, a second internal magnet 344 may also be installed on the pedicle on the opposite side of implant 340.

After installation of implant 340, external platform 350 may be placed on the patient's back 366 adjacent to the installed implant. Platform may be retained to the torso of the patient by a strap the circles the patient's waist or chest at the elevation of the implanted vertebrae 330. Platform 350 comprises a support 352 that adjustably holds first external magnet 360. First external magnet 360 is hung inside recess 364 by a plurality rods 354, which are fastened to external mounting plate 358 housing magnet 360. The angle and height of magnet 360 may be incrementally adjusted by adjustment member 356.

As illustrated in FIG. 21, external magnet 360 and internal magnet 342 may be positioned with facing positive poles (or facing negative poles) to generate a repulsive force between the platform 350 and the implant 340. The resulting magnetic force creates a rotational moment R on the vertebrae 330 to incrementally reorient the vertebrae 330 and diminish the abnormal rotation angle $\beta$. As vertebrae 330 rotates to a more normal orientation, the rest of the vertebrae of the spine follow.

If a second internal magnet 344 is installed opposite internal magnet 342, a second external magnet 362 may be positioned opposite internal magnet 344. As shown in FIG. 1, the opposing magnets may be positioned to generate an attractive force, thereby increasing the magnitude of the rotational moment R on the vertebrae.

In addition to effecting rotation of the spine, platform 350 may be oriented to correct for lateral curvature of the spine. By placing the platform 350 to the line up to the left of the implants, as shown in FIG. 21, a translational force T is created on the vertebrae 330 as a result of the attractive force between the second external magnet 362 and second internal magnet 344. In this configuration, external magnet 360 may be removed to increase the attractive force. The platform 350 may be incrementally repositioned to continue translation of the vertebrae 330.

3. Other Applications

Variations of the above embodiments could be use to gradually correct a variety of deformities. For example, pectus carinatum (a deformity of the chest involving a sternal protrusion) may be treated with the embodiments shown in FIGS. 14-17 and orienting the magnets to apply a repulsive rather than attractive force.

In another alternative embodiment, which may be beneficial for soft tissue deformities, a magnetic force discontinuously applied in order to accommodate blood flow to the tissue. For example, the force may be applied for a period of time (e.g. a minute) and then taken off for another period of time (applied in a pulsed fashion) in order to let blood flow back to the tissue being "reformed". In one embodiment illustrated in FIG. 22, a pulsed force field is generated by rotation of the external magnet 402 with respect to fixed internal magnet 402. The magnets may have magnetized quadrants 404 that repel/attract or become neutral upon a 90 degree rotation with respect to each other to achieve tension alternating with relaxation. In an alternative embodiment, the external magnet is moved closer and then farther from the internal magnet by rotating it on a cam (not shown).

In addition to magnetic force fields configured to manipulate body members by attraction of two magnets (e.g. the device above for repair of pectus excavatum), the magnets may be configured to provide a repulsive force (e.g. a magnetic Elizeroff to lengthen bone). In the embodiment illustrated in FIG. 23, internal repulsion device 410 comprises first member 414 partially encased in second member 412, wherein first member 414 is allowed to slide inside second member 412. Each member has a corresponding internal magnet 416, 418 which are configured to repel each other, thus forcing first member 414 to separate from second member 412 to form a "magnetic spring" to distance anatomy located on ends 420 and 422. The repulsive force may be varied by adjusting the position of magnets 418 and 416 away from ends 420 and 422.

Repulsion device 410 may be used in a variety of applications where gradual force may be applied to reposition or deform one or more body members. For example, device 410 may be disposed such that ends 420 and 422 are attached to two separate locations of a bone to lengthen or alter the shape of the bone.

In an alternative embodiment illustrated in FIG. 24, repulsion device 430 may be used having reservoir 434 and pump 436. Pump 436 may be positioned underneath the patient's skin 438, such that fluid may be directed through lead line 440 to reservoir 434 in second chamber 432. The pump may be used to increase the volume of reservoir 434, thereby distancing magnet 416 away from end 420 to incrementally increase the repulsive force between 416 and 418.

In another alternative embodiment illustrated in FIG. 25, repulsion device 450 comprises a mechanical jackscrew 470. The device has a first member 452 and second member 454 that apply a repulsive force to attachment points 456 and 458 that may be attached to one or more body members. Rotary magnet coupling 468 has an internal magnet 474 under the patient's skin 476 and a corresponding external magnet 472.

The magnets are polarized such that rotation of the external magnet 472 causes a proportional rotation in external magnet 474, which in turn rotates flexible shaft 478. Rotation of flexible shaft 478 is transferred to rotation of screw 462 located on first member 452 via worm gear 460. Nut 466 is attached to second member 454 and is threaded to screw 462 such that rotation of screw 462 causes the first member 452 to separate from 454. Additional force and separation may be achieved by further rotation of external magnet 474. Springs 464 may optionally be employed to create an additional pre-load between the first and second members.

FIG. 26 illustrates another alternative embodiment of a repulsion device 500 having an electric jackscrew. Control box 504 controls rotation of magnetic coupling 502. A signal is sent via wire 510 to electronics 512 to control electric motor 514, which drives rotation of screw 518 through gear reduction 516. Thus, a repulsive force may be incrementally applied to separate first member 524 from second member 522.

Although the description above contains many details, these should not be construed as limiting the scope of the invention but as merely providing illustrations of some of the presently preferred embodiments of this invention. For example, although the abovementioned embodiments primarily focus on pectus excavatum and scoliosis, the invention may be used on a variety of anatomical deformities. For example, pectus carinatum, scoliosis, club feet, cranial/facial anomalies or defects, skeletal dysplasias, cartilaginous deformities/dysplasias, and joint deformities/dysplasias may all be treated by the present invention. The invention may also be used to incrementally lengthen bone or apply bone compression to promote healing.

Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. An apparatus for incrementally manipulating the sternum of a patient, comprising:
   an implant adapted to be received on a location of the sternum, the implant responsive to a magnetic field;
   a platform configured to be positioned external to the patient; and a magnetic member coupled to the platform;

wherein the platform comprises a chest plate configured to rest on the patient's chest without subcutaneous fixation into the patient;

wherein the chest plate has a concave inner surface that is configured to be positioned substantially symmetrical sagittally across the sternum such that an apex of the concave inner surface lies substantially over the sternum when the platform is positioned over the chest;

wherein the magnetic member is positioned substantially coincident with respect to the apex;

wherein the magnetic member is configured to generate a magnetic force between the implant and the platform to incrementally manipulate the sternum;

wherein the concave inner surface of the chest plate is configured to allow the sternum to deform outwardly from the chest.

2. An apparatus as recited in claim 1, wherein the implant comprises a rare earth magnet.

3. An apparatus as recited in claim 1, wherein the magnetic member comprises a rare earth magnet.

4. An apparatus as recited in claim 1, wherein the implant and the magnetic member are configured to generate an attractive force between the implant and the platform.

5. An apparatus as recited in claim 4, wherein the chest plate is shaped such that the attractive force supports the chest plate symmetrically over the patient's chest.

6. An apparatus as recited in claim 5, further comprising a chest strap to support the chest plate to the patient's chest.

7. An apparatus as recited in claim 1, wherein the implant and the magnetic member are configured to generate a repulsive force between the implant and the platform.

8. An apparatus as recited in claim 1, wherein the magnetic force repositions the sternum.

9. An apparatus as recited in claim 1, wherein the magnetic force deforms the sternum.

10. An apparatus as recited in claim 9, wherein the magnetic force lengthens the sternum.

11. An apparatus as recited in claim 1, wherein the implant is adapted to be received on the sternum by fastening through to a posterior surface on the sternum.

12. An apparatus as recited in claim 11, wherein the implant comprises an internal magnet and casing to enclose the magnet.

13. An apparatus as recited in claim 12, further comprising:
a plurality of sutures;
wherein the sutures are configured to be looped through a plurality of holes in the implant casing and around the sternum.

14. An apparatus as recited in claim 11, wherein the implant comprises an array of rare earth magnets.

15. An apparatus as recited in claim 11, wherein the magnetic member comprises an array of rare earth magnets.

16. An apparatus as recited in claim 1, further comprising:
an adjustable stage coupled to the chest plate;
wherein the magnetic member is mounted on the stage.

17. An apparatus as recited in claim 16, further comprising a plurality of adjustment members coupled to the stage to adjust the angular orientation and position of the magnetic member with respect to the implant.

18. An apparatus as recited in claim 17, further comprising:
a plurality of sensors and a strain gauge coupled to the chest plate;
wherein the strain gauge is configured to measure the force applied to one or more locations on the platform.

19. An apparatus for incrementally manipulating the sternum of a patient, comprising:
an implant adapted to be received subcutaneously on a location of the sternum, the implant responsive to a magnetic field; and
means for generating an attractive force between the implant and a platform configured to be place external to the patient to manipulate the sternum;
wherein the attractive force is distributed by said generating means on the chest of the patient at laterally spaced apart locations from the implant;
said spaced apart locations being substantially equidistant on opposing sides of the sternum;
wherein the attractive force is configured to incrementally reposition the sternum anteriorly outward from the chest of the patient.

20. An apparatus as recited in claim 19, further comprising:
means for adjusting the magnitude of the magnetic force applied between the platform and the implant.

21. An apparatus as recited in claim 19, further comprising:
means for varying the direction of the magnetic force applied between the platform and the implant.

22. An apparatus as recited in claim 19, further comprising:
means for securing the implant to a location on the sternum.

23. An apparatus as recited in claim 22, wherein the implant is secured to the patient's sternum by fastening through to a posterior surface on the sternum.

24. An apparatus as recited in claim 19, further comprising:
means for detecting the force applied to the platform at a plurality of locations on the platform.

25. An apparatus as recited in claim 24, wherein the means for detecting the force applied to the platform comprises a strain gauge.

26. An apparatus as recited in claim 25, wherein the strain gauge is configured to measure the force at a plurality of locations on the platform.

27. An apparatus as recited in claim 25, further comprising a means for intermittently relieving the attractive force while the platform is maintained in place on the chest.

28. An apparatus as recited in claim 19; wherein the means for generating an attractive force comprises:
a chest plate configured to rest on the patient's chest without subcutaneous fixation into the patient;
wherein the chest plate has a concave inner surface that is configured to be positioned substantially symmetrical sagittally across the sternum such that an apex of the concave inner surface lies substantially over the sternum when the platform is positioned over the chest; and
a magnetic member positioned substantially coincident with respect to the apex;
wherein the magnetic member is configured to generate a magnetic force between the implant and the platform to incrementally manipulate the sternum;
wherein the concave inner surface of the chest plate is configured to allow the sternum to deform outwardly from the chest.

* * * * *